United States Patent
Hirvonen et al.

(10) Patent No.: US 11,938,341 B2
(45) Date of Patent: Mar. 26, 2024

(54) METHOD AND APPARATUS FOR FAST INFLUENCE MATRIX GENERATION

(71) Applicant: Siemens Healthineers International AG, Steinhausen (CH)

(72) Inventors: Petri Hirvonen, Espoo (FI); Matti Ropo, Helsinki (FI); Douglas Barnett, Palo Alto, CA (US); Timo Koponen, Helsinki (FI)

(73) Assignee: Siemens Healthineers International AG, Steinhausen (CH)

( * ) Notice: Subject to any disclaimer, the term of this patent is extended or adjusted under 35 U.S.C. 154(b) by 137 days.

(21) Appl. No.: 17/555,756

(22) Filed: Dec. 20, 2021

(65) Prior Publication Data
US 2023/0191150 A1 Jun. 22, 2023

(51) Int. Cl.
*A61N 5/10* (2006.01)

(52) U.S. Cl.
CPC ......... *A61N 5/1031* (2013.01); *A61N 5/1028* (2013.01); *A61N 2005/1034* (2013.01); *A61N 2005/1087* (2013.01)

(58) Field of Classification Search
None
See application file for complete search history.

(56) References Cited

U.S. PATENT DOCUMENTS

| 2017/0076671 A1 | 3/2017 | Kim et al. |
| 2017/0232274 A1* | 8/2017 | Isola ............... A61N 5/1045 600/1 |
| 2023/0256266 A1* | 8/2023 | Voronenko ......... A61N 5/1067 600/1 |

OTHER PUBLICATIONS

Mihaylov, I.B. et al.; "Analytic IMRT dose calculations utilizing Monte Carlo to predict MLC fluence modulation", Medical Physics, AIP, Melville, NY, US, vol. 33, No. 4, Mar. 10, 2006 (Mar. 10, 2006), pp. 828-839, XP012092067, ISSN: 0094-2405, DOI: 10.1118/1.2178449.
Extended European Search Report from European Application No. 22214472.7 dated May 12, 2023; 6 pages.

* cited by examiner

Primary Examiner — Hoon K Song
(74) Attorney, Agent, or Firm — Fitch, Even, Tabin & Flannery LLP

(57) ABSTRACT

These teachings provide for quickly yet accurately forming an influence matrix by generating the influence matrix via integration with a Monte Carlo particle transport simulation. The resultant influence matrix can then be utilized in an ordinary manner when optimizing a radiation treatment plan. By one approach, the foregoing comprises generating the influence matrix via integration with a Monte Carlo particle transport simulation on a particle-by-particle basis. For example, for each particle, these teachings can provide for identifying a spot to which the particle belongs and then adding a dose deposited by the particle during transport to an influence matrix element that corresponds to a spot to which the particle belongs and a voxel to where the dose was deposited.

10 Claims, 2 Drawing Sheets

METHOD AND APPARATUS FOR FAST INFLUENCE MATRIX GENERATION

TECHNICAL FIELD

These teachings relate generally to treating a patient's planning target volume with energy pursuant to an energy-based treatment plan and more particularly to generating an influence matrix.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called energy-based treatment plan often serves in the foregoing regards.

An energy-based treatment plan such as a radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Influence matrices find use in at least some optimization techniques. This is particularly so for proton therapy optimization. In proton therapy, protons are often divided into spots, i.e., beams with narrow distributions of position, direction, and energy. A corresponding transport volume, on the other hand, is discretized into a three-dimensional rectilinear grid of voxels. An influence matrix maps each spot's contribution to each voxel's dose with unit weight. The dose at each voxel can be obtained simply by multiplying the influence matrix with a vector of spot weights. This ease of use finds ready application and use when optimizing a corresponding radiation treatment plan.

Calculating the dose in this way is much faster than with many other techniques, but unfortunately generating the influence matrix in the first instance is very computationally intensive and time consuming. This is because one needs to consider, typically, billions of contributions from thousands of spots to millions of voxels.

BRIEF DESCRIPTION OF THE DRAWINGS

The above needs are at least partially met through provision of the method and apparatus for fast influence matrix generation described in the following detailed description, particularly when studied in conjunction with the drawings, wherein.

Figure 1:
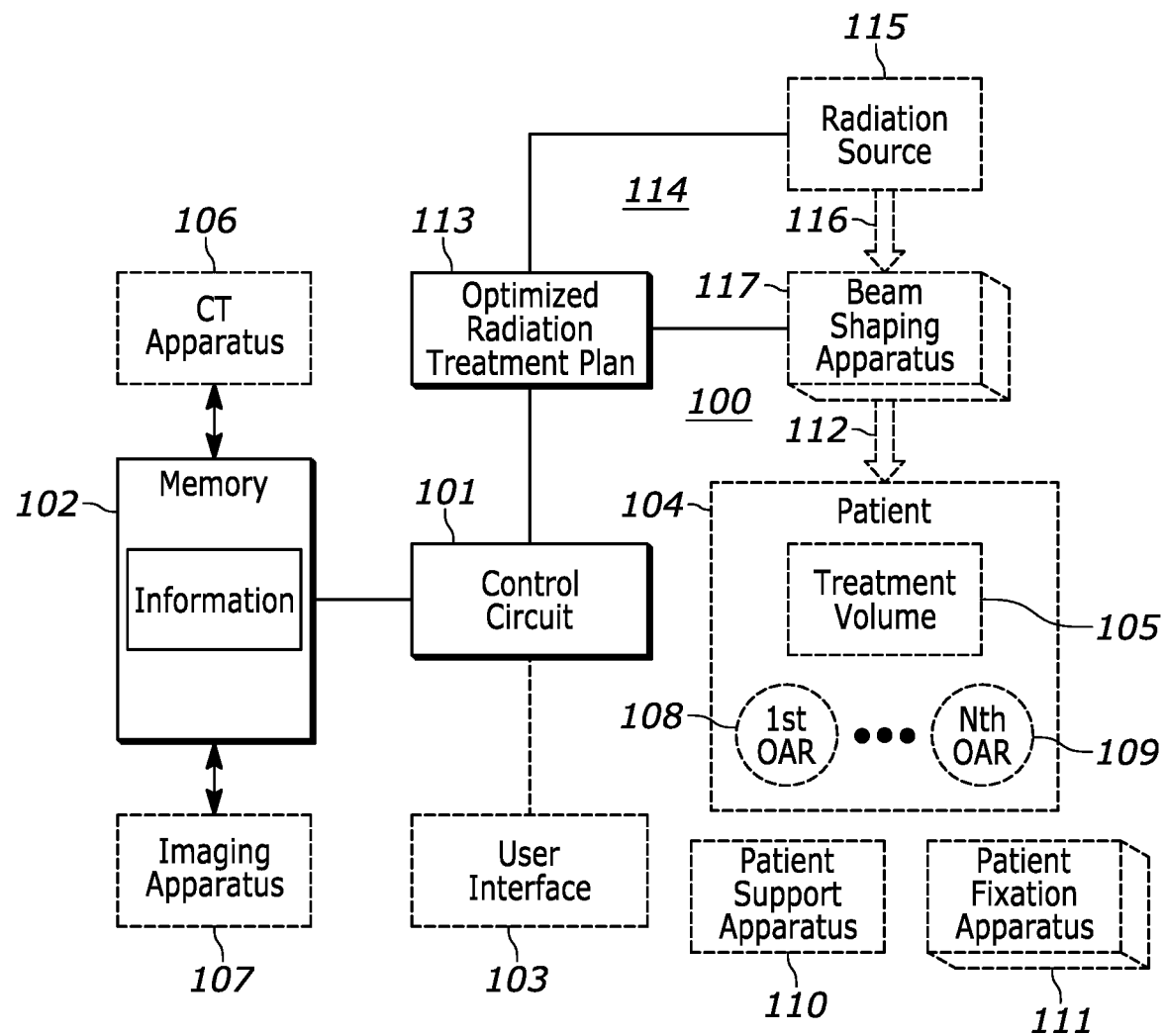
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate optimizing a patient treatment plan to administer therapeutic energy, such as a proton beam, to a particular patient.

By one approach, these teachings provide for quickly yet accurately forming an influence matrix by generating the influence matrix via integration with a Monte Carlo particle transport simulation. The resultant influence matrix can then be utilized in an ordinary manner when optimizing a radiation treatment plan.

By one approach, the foregoing comprises generating the influence matrix via integration with a Monte Carlo particle transport simulation on a particle-by-particle basis. For example, for each particle, these teachings can provide for identifying a spot to which the particle belongs and then adding a dose deposited by the particle during transport to an influence matrix element that corresponds to a spot to which the particle belongs and a voxel to where the dose was deposited.

Generally speaking, generating the influence matrix via integration with a Monte Carlo particle transport simulation can comprise calculating the influence matrix together with calculation of an administered dose. This can include multiplying deposited energy values by a precomputed inverse of a corresponding spot weight and then adding a corresponding dose contribution to an influence matrix element that correlates to a corresponding spot in a voxel. These teachings can also include, when calculating the influence matrix together with calculation of an administered dose, and following transport, multiplying each nonzero influence matrix element by a precomputed inverse of a corresponding voxel mass.

By greatly reducing the amount of time and/or computational capacity typically associated with generating an influence matrix, these teachings can greatly reduce the amount of time (often by many orders of magnitude) that is typically associated with at least some radiation treatment plan optimization procedures. In addition, by significantly reducing that time/resource requirement to generate an influence matrix, these teachings make feasible the use of influence matrices in other contexts that were previously not practical to consider.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as radiation dosing information, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan 113 (such as, for example, an optimized radiation treatment plan). This energy-based treatment plan 113 typically comprises specified values for each of a variety of treatment-platform parameters during each of a plurality of sequential exposure fields. In this case the energy-based treatment plan 113 is generated through an optimization process. Various automated optimization processes specifically configured to generate such an energy-based treatment plan are known in the art. As the present teachings are not overly sensitive to any particular selections in these regards, further elaboration in these regards is not provided here except where particularly relevant to the details of this description.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses.

In a typical application setting the energy-based treatment platform 114 will include an energy source 115 such as a source of ionizing radiation, a source of microwave energy, a source of heat energy, and so forth. For the sake of an illustrative example, it will be presumed here that the energy source 115 is a source of protons that provides a beam of protons to irradiate diseased tissue.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the energy source 115, and one or more energy-shaping apparatuses 117 (for example, beam-shaping apparatuses such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction)

during an energy-based treatment session by the control circuit 101. As the foregoing elements and systems are well understood in the art, further elaboration in these regards is not provided here except where otherwise relevant to the description.

Figure 2:
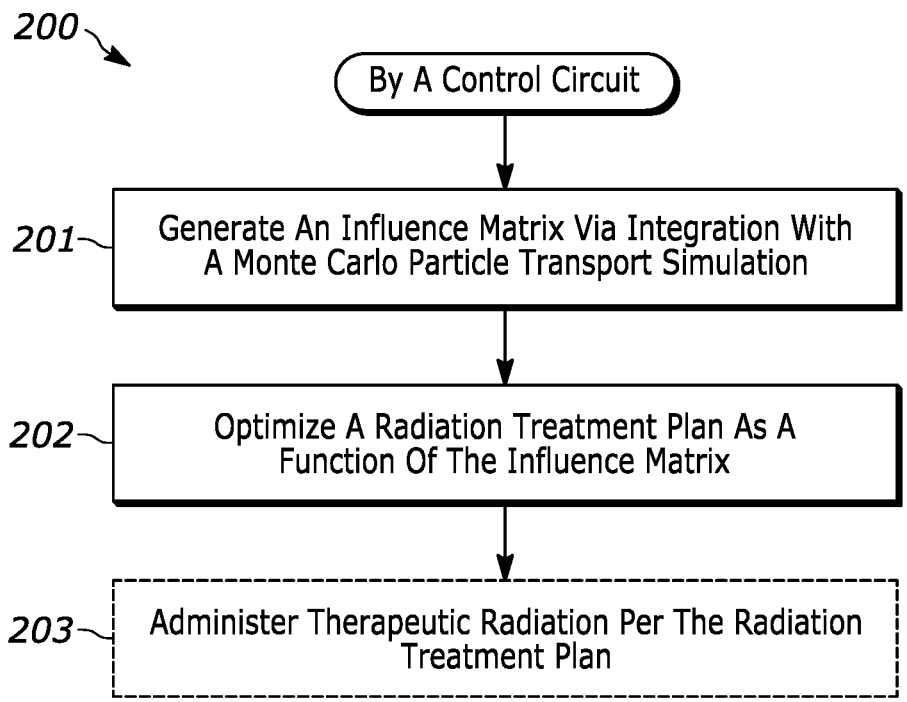
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described.

At block 201, this process 200 provides for generating an influence matrix via integration with a Monte Carlo particle transport simulation.

It may be helpful to some readers to briefly recount some details regarding Monte Carlo particle transport simulation. The dose deposited in a medium by radiation of ionizing particles such as photons, electrons, protons, or neutrons can be solved using Monte Carlo particle transport simulations. This is of great interest in radiation therapy treatment planning for modelling dose distributions in patients' tissues. In Monte Carlo transport, a very large number of random particles are sampled whose initial position and initial velocity distributions match the radiation source being modeled. This batch of primary particles is then propagated in a medium in a stepwise fashion where they experience interactions with the medium deflecting them and slowing them down. As the particles slow down, they deposit energy, i.e., dose, to the medium. Primary particles can also deflect off further, secondary particles to be tracked. Monte Carlo transport can give more accurate estimates of the dose deposited compared to, for example, fluence-based dose calculation methods.

These teachings provide for speeding up influence matrix calculations by integrating the former into a Monte Carlo dose calculation algorithm at a low level. This can comprise, for each particle, identifying the spot to which the particle belongs to and, when the particle is transported, the dose the particle deposits during transport is added to the influence matrix element corresponding to the spot to which the particle belongs and the voxel in which the dose was deposited. This approach dramatically eliminates much of the usually-expected time/resource overhead requirements when calculating an influence matrix.

Stated somewhat differently, these teachings provide for recording the spot each particle belongs to and, as the particle p is transported and deposits its energy to the medium, this contribution is added to the influence matrix element Msv that corresponds to the spot s the current particle belongs to and to the voxel v the particle is in. Such a contribution is given by $$\Delta M_{sv} = \frac{\Delta E_p}{w_s m_v}$$

where $\Delta E_p$ is the energy deposited by the particle, $w_s$ is the weight of the spot the particle belongs to, $m_v$ is the voxel mass given by its volume $V_v$, and the local density $d_v$ ($m_v = d_v V_v$).

Figure 3:
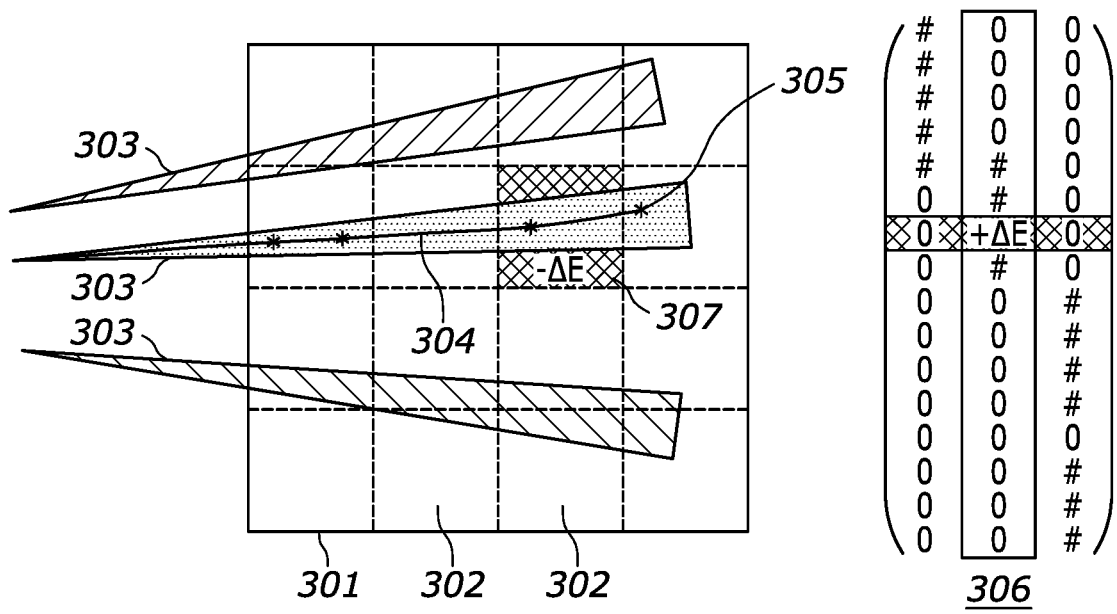
FIG. 3 comprises a schematic representation as configured in accordance with various embodiments of these teachings.

FIG. 3 helps to illustrate the foregoing. The depicted grid 301 corresponds to a two-dimensional patient comprising 4×4 voxels (two of which are denoted by reference 302). The wedges 303 are proton beams or "spots," and the broken line 304 is the trajectory of an individual proton inside the patient. The stars (one of which is denoted by reference 305) indicate collisions of the proton with particles in the medium where it loses and deposits some energy (where "dose" equals energy divided by local density).

Reference numeral 306 denotes the corresponding influence matrix. In this illustrative example the columns of the influence matrix each correspond to one spot and each row corresponds to one voxel. Reference numeral 307 corresponds to a particular voxel that is under present consideration. The energy ΔE deposited by the particle in the trajectory denoted by reference numeral 304 to that particular voxel 307 is added to the influence matrix shown on the right as illustrated.

Calculating the influence matrix together with the dose can involve the following changes:

First, during transport, the deposited energy $\Delta E_p$ can be multiplied by the precomputed inverse of the spot weight $1/w_s$. (When the dose is calculated with unit spot weights ($w_s = 1$), this cost can be avoided.) This contribution is added to the influence matrix element $M_{sv}$ corresponding to the spot s and to the voxel v. (If desired, and if the current, primary particle kicks off a secondary particle during transport, the spot the former belongs to can be assigned to the latter as well.)

After transport, each nonzero influence matrix element $M_{sv}$ can be multiplied by the precomputed inverse of the voxel mass $1/m_v$. (It will be appreciated that performing this step after transport and not earlier means that each nonzero element need be multiplied only once with $1/m_v$ (as compared to every time any of the many particles belonging to spot s deposits dose to voxel v.)

Many, and often most, influence matrix elements are zeros or negligibly small. This is due to many voxels corresponding to air and to many voxels being located nowhere near a particular spot. Using a compressed data structure for the influence matrix that does not waste memory for this large number of unnecessary elements can, in some cases, allow for the use of a slower, less expensive, storage device. One data structure candidate is a sparse matrix.

These teachings will support the use of distributed processing if desired. For example, one can distribute the Monte Carlo transport, the influence matrix calculation, and the subsequent optimization or other step(s) amongst a plurality of remote servers. For example, each spot and a corresponding narrow slice of the target can be handled by a different device. In such a case, each server can update the influence matrix elements according to their respective assigned spots.

Those skilled in the art will recognize that a wide variety of modifications, alterations, and combinations can be made with respect to the above-described embodiments without departing from the scope of the invention. Accordingly, such modifications, alterations, and combinations are to be viewed as being within the ambit of the inventive concept.

What is claimed is:

1. A method comprising:
   by a control circuit:
   generating an influence matrix via integration with a Monte Carlo particle transport simulation by generating the influence matrix via integration with a Monte Carlo particle transport simulation on a particle-by-particle basis by, for each of the particles:
   identifying a spot to which the particle belongs; and
   adding a dose deposited by the particle during transport to an influence matrix element that corresponds to a spot to which the particle belongs and a voxel where the dose was deposited;
   optimizing a radiation treatment plan for proton therapy as a function of the influence matrix.

2. A method comprising:
by a control circuit:
generating an influence matrix via integration with a Monte Carlo particle transport simulation by calculating the influence matrix together with calculation of an administered dose by multiplying deposited energy values by a precomputed inverse of a corresponding spot weight.

3. The method of claim 2, wherein calculating the influence matrix together with calculation of an administered dose further comprises adding a corresponding dose contribution to an influence matrix element that correlates to a corresponding spot and voxel.

4. The method of claim 3, wherein calculating the influence matrix together with calculation of an administered dose further comprises, when a current particle interacts with a secondary particle during transport, assigning a spot corresponding to the current particle to the secondary particle as well.

5. The method of claim 2, wherein calculating the influence matrix together with calculation of an administered dose further comprises, following transport, multiplying each nonzero influence matrix element by a precomputed inverse of a corresponding voxel mass.

6. An apparatus comprising:
a control circuit configured to:
generate an influence matrix via integration with a Monte Carlo particle transport simulation by generating the influence matrix via integration with a Monte Carlo particle transport simulation on a particle-by-particle basis by, for each of the particles:
identifying a spot to which the particle belongs; and
adding a dose deposited by the particle during transport to an influence matrix element that corresponds to a spot to which the particle belongs and a voxel where the dose was deposited;
optimize a radiation treatment plan for proton therapy as a function of the influence matrix.

7. An apparatus comprising:
a control circuit configured to:
generate an influence matrix via integration with a Monte Carlo particle transport simulation by calculating the influence matrix together with calculation of an administered dose by multiplying deposited energy values by a precomputed inverse of a corresponding spot weight.

8. The apparatus of claim 7, wherein the control circuit is further configured to calculate the influence matrix together with calculation of an administered dose by adding a corresponding dose contribution to an influence matrix element that correlates to a corresponding spot and voxel.

9. The apparatus of claim 8, wherein the control circuit is further configured to calculate the influence matrix together with calculation of an administered dose by, when a current particle interacts with a secondary particle during transport, assigning a spot corresponding to the current particle to the secondary particle as well.

10. The apparatus of claim 7, wherein the control circuit is further configured to calculate the influence matrix together with calculation of an administered dose by, following transport, multiplying each nonzero influence matrix element by a precomputed inverse of a corresponding voxel mass.

* * * * *